United States Patent [19]

Morris et al.

[11] 4,265,120

[45] May 5, 1981

[54] FATIGUE DETECTION UTILIZING ACOUSTIC HARMONICS

[75] Inventors: Winfred L. Morris, Thousand Oaks; Richard V. Inman, Simi Valley; Otto Buck, Thousand Oaks, all of Calif.

[73] Assignee: Rockwell International Corporation, El Segundo, Calif.

[21] Appl. No.: 41,671

[22] Filed: May 23, 1979

[51] Int. Cl.³ .............................................. G01N 29/04
[52] U.S. Cl. ................................................... 73/600
[58] Field of Search ................. 73/574, 577, 579, 589, 73/596, 599, 600

[56] References Cited

U.S. PATENT DOCUMENTS 2,847,853   8/1958   Rankin .................................... 73/599

OTHER PUBLICATIONS

"Harmonic Generation for Measurement of Internal Stresses as Produced by Dislocations" by Buck, IEEE Transactions on Sonics and Ultrasonics vol. SU–23, No. 5, Sep. 1976.

*Primary Examiner*—James J. Gill
*Attorney, Agent, or Firm*—H. Fredrick Hamann; Craig O. Malin; John J. Deinken

[57] ABSTRACT

Disclosed is a nondestructive test method for inspecting an object, including the steps of generating a surface acoustic wave at a first location on the object, detecting a harmonic of the generated wave at a second location on the object, and relating the characteristics of the detected wave to the remaining useful life of the object. The amplitude of the detected harmonic may be compared to standard amplitude values to predict the percentage of fatigue life remaining in the object, or the amplitude may be used to estimate the size and density of cracks in the object. Additionally, the harmonic wave may be detected for a range of stress values, the amplitude differential between the maximum harmonic amplitude and the minimum amplitude under compression calculated, and the differential related to the remaining useful life of the object.

12 Claims, 4 Drawing Figures

FATIGUE DETECTION UTILIZING ACOUSTIC HARMONICS

STATEMENT OF GOVERNMENT INTEREST

The invention herein described was made in the course of or under a contract with the Department of the Air Force.

BACKGROUND OF THE INVENTION

This invention is related to nondestructive testing methods and, more particularly, to acoustic methods for evaluating the fatigue life of materials.

The development of increasingly higher performance requirements and the need to carefully control building costs have frequently led to the design of modern structures in accordance with a "safe life" or "damage tolerant" philosophy. In this approach, structural components are specified with dimensions calculated so that fatigue cracks and resulting damage will not progress to a catastrophic level prior to detection at scheduled inspection periods. This design procedure recognizes that no part is likely to be perfect or remain so during its intended lifetime of use.

Thus, under modern design practices, a flaw of a subcritical size must be assumed to be present in the structure. The upper limit of this flaw's size is determined by the sensitivity of the inspection system to be used, at a 100% confidence level for detection of the flaw. At the present time, the sensitivity of nondestructive evaluation (NDE) methods recognized in the art, such as the dye penetrant, magnetic particle, ultrasonic, eddy current, and radiographic inspection methods, is generally considered to be approximately 1 mm. Thus, for example, if it is assumed that no surface flaw larger than 1 mm has escaped detection during inspection, and if it is further assumed that a very simple tension-tension fatigue load of constant amplitude is applied to the structure, the remaining life of the part, or the minimum number of remaining cycles to failure $\Delta N$, can be estimated by interpretation of the "Paris equation":

$$da/dN = A(\Delta K)^m \qquad (1)$$

where $da/dN$ is the rate of crack growth, $\Delta K$ is the stress intensity range, and A and m are constants for a particular material. Further manipulation of this expression, together with some simple assumptions, can be performed to derive an expression for the critical material dependent flaw size. Table I lists some estimated critical flaw sizes for several important structural materials.

TABLE I.

Order of Magnitude Estimates of Critical Flaw Sizes in Some Structural Alloy.

| | Materials | Critical Flaw Size (mm) |
|---|---|---|
| Steels | 4340 | 1.5 |
| | D6AC | 2.3 |
| | Marage 250 | 4.2 |
| | 9Ni4Co 20C | 27.5 |
| Aluminum Alloys | 2014-T651 | 8.0 |
| | 2024-T3 | 27.5 |
| Titanium Alloys | 6A1-4V | 8.0 |

It is a basic goal of all major nondestructive evaluation programs to determine the size, shape, and orientation of subcritical defects, with all three parameters being equal in importance. As can be seen from Table I, however, some of the critical flaw sizes, even for metals, are quite small. Since the sensitivity of standard NDE techniques is limited to no less than approximately 1 mm, it is apparent that in some materials, a flaw may approach the critical size before it can be effectively detected by present NDE methods.

Consequently, a need has developed in the art for an NDE technique which is capable of detecting flaws or fatigue damage with a much higher sensitivity, i.e, much earlier in the fatigue life of an object, than is possible with known techniques. Critical components whose life is controlled by fatigue, for example, are at the present time considered in some structural applications to have failed as soon as the probability of forming a crack of a small but finite size is 0.1%. Regardless of whether or not such a crack actually exists in a particular component, the component is retired automatically. With a more precise NDE technique, however, each such component could be inspected upon reaching the 0.1% probability level, and only those particular parts whose inspection revealed unacceptably large cracks would be retired. The latter approach, known as "retirement for cause", would be much more economical, but could provide the same level of reliability as prior art techniques.

SUMMARY OF THE INVENTION

It is a general object of the present invention to provide an improved acoustic method for the fatigue testing of materials.

A nondestructive test method for inspecting an object, according to this invention, includes the steps of:
(a) generating an acoustic wave at a first location on the object;
(b) detecting a harmonic of the generated wave at a second location on the object; and
(c) relating the characteristics of the detected wave to the remaining useful life of the object.

In a more particular embodiment, a surface acoustic wave is generated, the second harmonic is detected, and the amplitude of the detected harmonic is compared to standard amplitude values, for test samples having known fatigue histories, to predict the percentage of fatigue life remaining in the object. Alternatively, the amplitude of the detected harmonic is utilized to estimate the size and density of existing cracks in the object.

In another embodiment, the method according to this invention includes the steps of:
(a) generating an acoustic wave at a first location on the object;
(b) stressing the object;
(c) detecting a harmonic of the generated wave at a second location on the object;
(d) repeating steps (b) and (c) for a range of stress values;
(e) calculating the amplitude differential between the maximum harmonic amplitude detected and the minimum amplitude under compression; and
(f) relating the calculated differential to the remaining useful life of the object.

In a more particular embodiment, a surface acoustic wave is generated, the second harmonic is detected, and the calculated differential is compared to standard differential values, for test samples having known fatigue histories, to predict the percentage of fatigue life remaining in the object. Alternatively, the size and density of existing cracks in the object may be estimated from the calculated differential.

Examples of the more important features of the invention have been broadly outlined in this summary in order to facilitate an understanding of the detailed description that follows and so that the contributions which this invention provides to the art may be better appreciated. There are, of course, additional features of the invention, which will be described below and which are included within the subject matter of the appended claims.

BRIEF DESCRIPTION OF THE DRAWINGS

Additional objects, features, and advantages of the present invention will become apparent by referring to the detailed description below of the preferred embodiments in connection with the accompanying drawings, wherein like reference numerals refer to like elements throughout all the figures. In the drawings.

DESCRIPTION OF THE PREFERRED EMBODIMENTS

Scanning electron microscope studies on smooth specimens of certain high strength aluminum alloys have led to the development of a simplified description of the origination of surface microcracks in structural materials under fatigue conditions. An outline of this description is presented in Table II. The failure sequence described in Table II pertains to low cycle fatigue (i.e., involving a large cyclic stress amplitude) for those alloys. It has been observed that in certain materials microcrack nucleation originates primarily in brittle intermetallic particles. After nucleation, the microcracks grow into the matrix, interact with the grain boundaries, and eventually coalesce with other microcracks to form a macrocrack whose subsequent growth terminates the life of the specimen.

TABLE II.

Development of Microcracks in a Smooth, High-Strength Aluminum Alloy

| Percentage of Expended Fatigue Life | Stage of Failure | Mean Crack Size |
| --- | --- | --- |
| 0 | Cracking inside inter- | 10–20 $\mu$m |
| 10 | metallic particles | |
| 20 | | |
| 30 | Crack propagation out | 20–100 $\mu$m |
| 40 | of intermetallics | |
| 50 | | |
| 60 | Crack interaction with | 100 $\mu$m |
| 70 | grain boundaries | |
| 80 | Crack coalescence | 500 $\mu$m |
| 90 | | |
| 100 | Failure | Specimen Dimension |

Where the specimen is subjected to large cyclic amplitudes, the surface density of such cracks prior to the formation of a terminal crack can exceed $10^4/cm^2$.

It is an outstanding feature of the present invention to provide a method utilizing the growth of such cracks to determine the remaining useful life in a fatigued object. Fatigue microcracks are known to be partially open under unstressed conditions. This unbonded interface presents a mechanism for enhancing the generation of harmonics when an acoustic wave is transmitted through a material containing such cracks. Theoretically, the harmonic amplitude developed by the opening and closing of such an interface in the presence of an acoustic wave will be strongly dependent upon the external applied stress normal to the interface. As an external tensile stress, $\sigma$, is applied, the crack will progressively open, while a sufficient compressive load will fully close the crack. At either extreme of fully open or fully closed, the generation of harmonics by this mechanism will be expected to cease.

Figure 1:
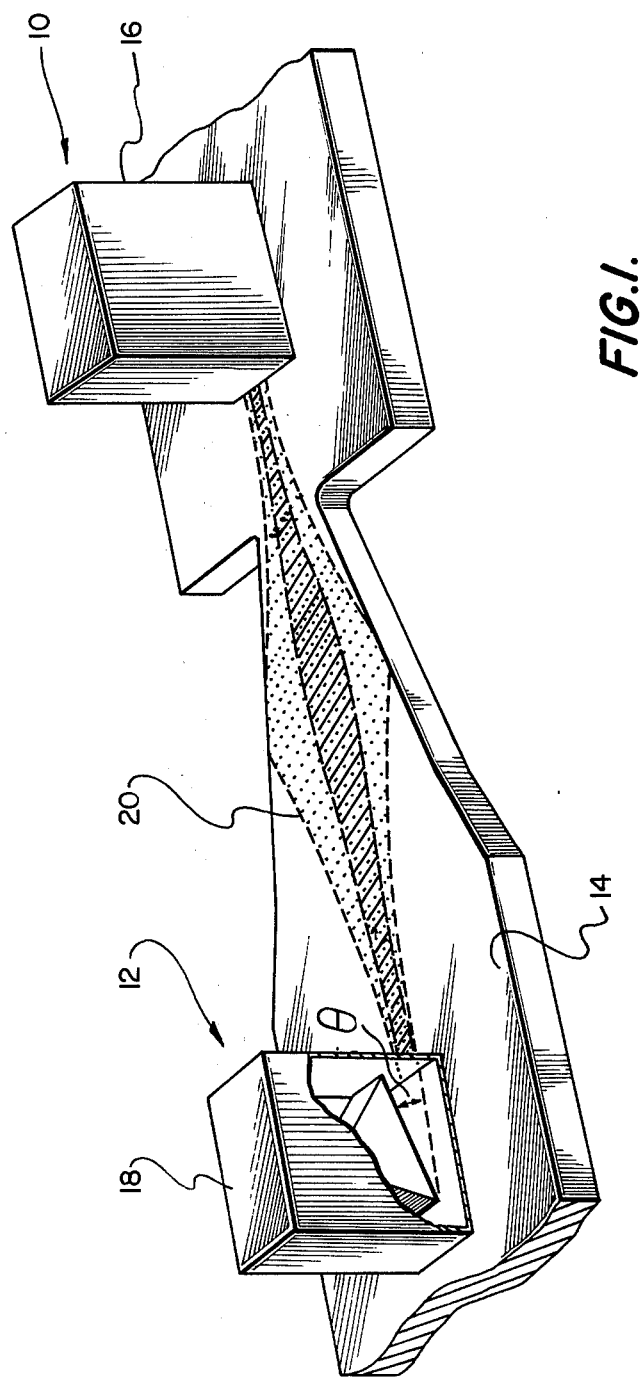
FIG. 1 is a perspective view of a test arrangement which may be utilized to practice the present invention.

One suitable test configuration for practicing the invention is illustrated in a perspective view in FIG. 1, in which a 5 MHz transmitting transducer 10 and a 10 MHz receiving transducer 12 are positioned on a test object 14. A tapered flexural fatigue specimen geometry is employed in the object 14, in order to generate a uniform surface stress, and thus a homogeneous density of fatigue cracks, across the gauge section of the object 14. For the particular test results illustrated in the drawings, FIGS. 3 and 4, the specimens used were aluminum 7075-T6, which specimens were given a mechanical surface polish and fatigued in stroke control. A strain gauged arm in the load train was used to measure the applied bending moment, from which the surface stress was calculated.

The transducers 10 and 12, of the PZT type, are mounted outside the gauge section onto fused quartz wedges. The wedge angle $\theta$, measured relative to the specimen surface, is adjusted for optimum transmission and reception of surface acoustic waves. Bottomless boxes 16 and 18, containing the transducers, are attached to the specimen 14 using an acyritate cement and then filled with water to acoustically couple the specimen and the transducers. The approximate area on the specimen from which the high amplitude portion of the 10 MHz harmonic is received is outlined by the dotted line 20.

Figure 2:
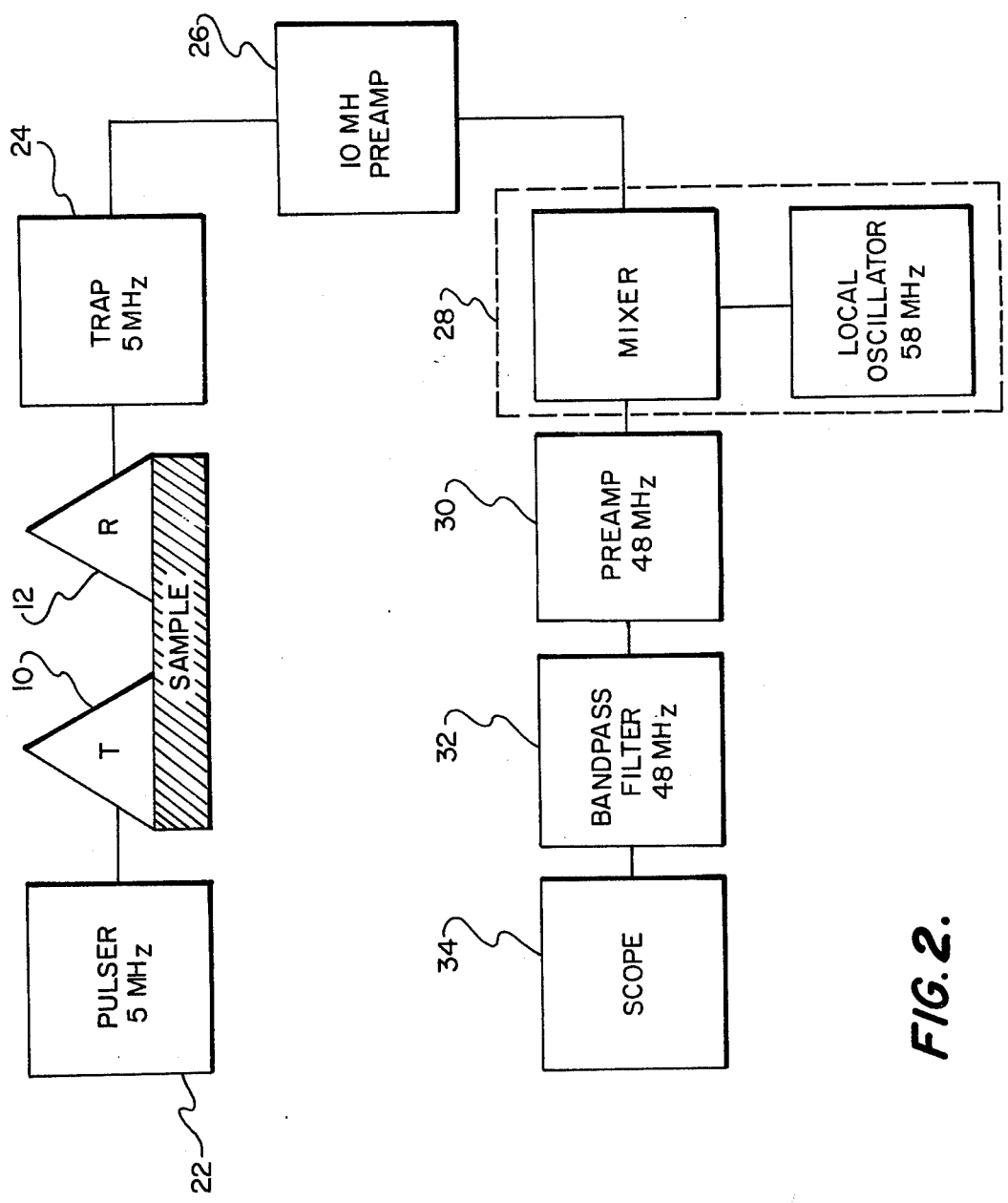
FIG. 2 is a schematic block diagram of the apparatus utilized in the arrangement of FIG. 1.

Now referring to FIG. 2, an electronics block diagram is provided illustrating the circuitry employed with the apparatus of FIG. 1 to practice the method of this invention. A 5 MHz pulser 22 is used in conjunction with the transducer 10 to produce fundamental frequency acoustic pulses of approximately 1 $\mu$sec in length. The second harmonic is received by the 10 MHz transducer 12. A tuned trap 24, following the receiving transducer 12, prevents any overload of the receiving electronics by the 5 MHz signal. The harmonic signal is then amplified by a 10 MHz preamplifier 26, routed to a heterodyne receiver 28, amplified by a preamplifier 30, filtered in a bandpass filter 32, and finally displayed on an oscilloscope 34.

The amplitude of the fundamental signal for an unfatigued specimen has been found to be essentially independent of the applied stress. A small variation in the received second harmonic amplitude, however, has been observed as a function of the external loading. These harmonic signals resulted from the nonlinear mechanical properties of the alloy tested. Therefore, all changes in the second harmonic amplitude with fatigue should be analyzed relative to the amplitude of harmonic generation for the unfatigued sample at the same surface stress.

Figure 3:
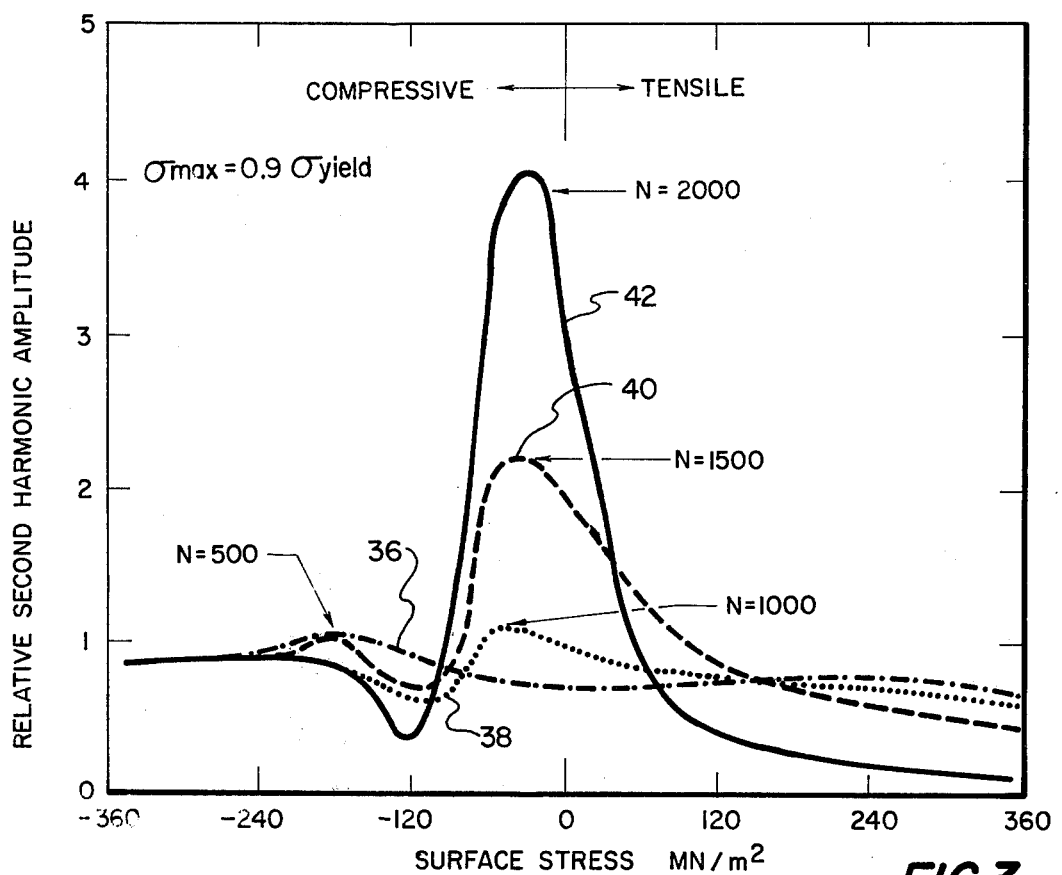
FIG. 3 is a graphical representation illustrating the variation in amplitude of a second harmonic signal with changes in stress and fatigue in the host material.
Figure 4:
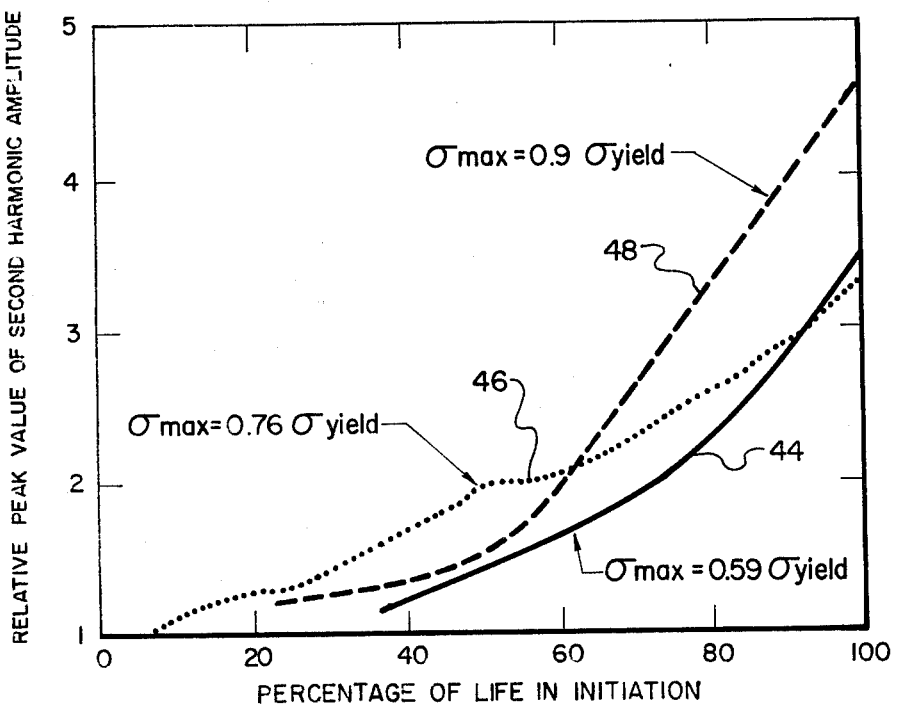
FIG. 4 graphically depicts the increase in amplitude of a second harmonic signal with increasing fatigue, for various maximum stress values.

In a particular example of the use of the present invention, 10 MHz harmonic measurements were made on aluminum 7075-T6 specimens which were fatigued at maximum cyclic surface stresses, $\sigma_{max}$, of 59, 76, and 90% of the materials yield strength, $\sigma_{yield}$, which for this alloy is 400 MN/m². Typical results for measurements at $\sigma_{max}$ of 0.9 $\sigma_{yield}$ are illustrated in FIG. 3. Plotted as a function of surface stress is the relative second harmonic amplitude, i.e., the ratio of the amplitude after N fatigue cycles to the amplitude prior to fatigue at the same surface stress. Plotted in FIG. 3 are four curves 36, 38, 40, and 42, which correspond to measurements made after 500, 1000, 1500, and 2000 fatigue cycles, respectively. The central feature of the data plotted in FIG. 3 is a second harmonic signal whose maximum increases with N at a slightly compressive stress. The same general character of the second harmonic response to the applied stress level has been found at all cyclic surface stresses which have been used to fatigue test specimens. These results are summarized in FIG. 4, where the peak value of the relative second harmonic amplitude is plotted as a function of the percentage of expended life in the crack initiation phase of fatigue, where the period of life in initiation is defined as that part of the total life necessary to produce the first surface crack having a length of approximately 0.5 mm. The three plotted curves 44, 46, and 48 correspond to maximum cyclic surface stresses of 0.59, 0.76, and 0.9 of the yield strength, respectively.

One method for determining the fatigue life of an object, according to this invention, is to measure test samples made from the same material as the object for the second harmonic amplitude, the test samples having been subjected to a variety of known fatigue histories. The harmonic amplitudes for the test samples are measured at a constant stress level, such as no external stress or a slightly compressive stress. The object to be tested is then measured for the second harmonic at the same stress. The latter amplitude value is compared to those for the known test samples to predict the percentage of fatigue life remaining in the object.

In an alternative method, a set of calibration curves is prepared by measuring the harmonic amplitude as a function of stress for a number of standard samples having known microcracking damage. Similar measurements are performed on the test object. The amplitude differential, between the maximum harmonic amplitude and the minimum amplitude under a compressive stress for the object, is compared to similar differentials for the calibration curves. The amplitude differential can then be matched to the closest calibration value to predict the percentage of fatigue life remaining in the object, which is related to the crack density in the object.

In summary, the harmonic generation fatigue detection technique of this invention offers a highly sensitive detection method. For $\sigma_{max}=0.9$ $\sigma_{yield}$, for example, the fraction of fatigue lifetime spent in initiation of the first 0.5 mm surface microcrack is in excess of 90% of the total fatigue lifetime of a material. Although a 0.5 mm crack is about the smallest surface crack which can be detected with conventional nondestructive testing techniques, harmonic signals can be detected with the present invention much earlier in the fatigue life of an object. Such harmonic signals are associated with microcracking densities on the order of 100/cm² with mean lengths of 15-20 $\mu$m. Furthermore, the acoustic harmonic approach detects an integrated signal which is derived from contributions by all the microcracks in the area inspected. Because the method measures the nonlinear elastic response of a fatigue damaged surface, it is comparatively insensitive to background noise problems arising from the presence of surface roughness caused by machining.

In conclusion, although typical embodiments of the present invention have been illustrated and discussed above, numerous modifications and alternative embodiments of the method of this invention will be apparent to those skilled in the art in view of this description. Accordingly, this description is to be considered as illustrative only and is provided for the purpose of teaching those skilled in the art the manner of performing the method of this invention. Furthermore, it should be understood that the forms of the invention depicted and described herein are to be considered as the presently preferred embodiments. Various changes may be made in the configurations, sizes, and arrangements of the components of the invention, as will be recognized by those skilled in the art, without departing from the scope of the invention. Equivalent elements, for example, might be substituted for those illustrated and described herein, parts or connections might be reversed or otherwise interchanged, and certain features of the invention might be utilized independently of the use of other features, all as will be apparent to one skilled in the art after receiving the benefit attained through reading the above description of the invention.

What is claimed is:

1. A nondestructive test method for inspecting an object, comprising the steps of:
   (a) generating an acoustic wave at a first location on the object;
   (b) detecting a harmonic of the generated wave at a second location on the object; and
   (c) relating the characteristics of the detected wave to the surface cracks present in the object to provide an indication of the remaining useful life of the object.

2. The method of claim 1, wherein step (c) further comprises comparing the amplitude of the detected harmonic to standard amplitude values, for test samples having known fatigue histories, to predict the percentage of fatigue life remaining in the object.

3. The method of claim 1, wherein step (c) further comprises estimating from the amplitude of the detected harmonic the size and density of existing cracks in the object.

4. The method of claim 1, wherein step (b) further comprises detecting the second harmonic of the generated wave.

5. The method of claim 1, wherein the acoustic wave generated is a surface acoustic wave.

6. A nondestructive test method for inspecting an object, comprising the steps of:
   (a) generating a surface acoustic wave at a first location on the object;
   (b) detecting the second harmonic of the generated wave at a second location on the object; and
   (c) comparing the amplitude of the detected harmonic to standard amplitude values, for test samples having known fatigue histories, to predict the percentage of fatigue life remaining in the object.

7. A nondestructive test method for inspecting an object, comprising the steps of:

(a) generating an acoustic wave at a first location on the object;
(b) stressing the object;
(c) detecting a harmonic of the generated wave at a second location on the subject;
(d) repeating steps (b) and (c) for a range of stress values;
(e) calculating the amplitude differential between the maximum harmonic amplitude detected and the minimum amplitude under compression; and
(f) relating the calculated differential to the remaining useful life of the object.

8. The method of claim 7, wherein step (f) comprises comparing the calculated differential to standard differential values, for test samples having known fatigue histories, to predict the percentage of fatigue life remaining in the object.

9. The method of claim 7, wherein step (f) comprises estimating from the calculated differential the size and density of existing cracks in the object.

10. The method of claim 7, wherein step (c) further comprises detecting the second harmonic of the generated wave.

11. The method of claim 7, wherein the acoustic wave generated is a surface acoustic wave.

12. A nondestructive test method for inspecting an object, comprising the steps of:
(a) generating a surface acoustic wave at a first location on the object;
(b) stressing the object;
(c) detecting the second harmonic of the generated wave at a second location on the object;
(d) repeating steps (b) and (c) for a range of stress values;
(e) calculating the amplitude differential between the maximum harmonic amplitude detected and the minimum amplitude under compression; and
(f) comparing the calculated differential to standard differential values, for test samples having known fatigue histories, to predict the percentage of fatigue life remaining in the object.

* * * * *